(12) United States Patent
Infante et al.

(10) Patent No.: US 10,952,924 B2
(45) Date of Patent: Mar. 23, 2021

(54) LIP AUGMENTATION ASSEMBLY AND METHOD OF SELECTIVELY PLUMPING SEGMENTS OF THE LIPS

(71) Applicant: Indiga Group, Inc., Fort Lauderdale, FL (US)

(72) Inventors: Lilita Infante, Hollywood, FL (US); Jonathan Osborne, Fort Lauderdale, FL (US)

(73) Assignee: Indiga Group, Inc., Fort Lauderdale, FL (US)

( * ) Notice: Subject to any disclaimer, the term of this patent is extended or adjusted under 35 U.S.C. 154(b) by 0 days.

(21) Appl. No.: 16/352,811

(22) Filed: Mar. 13, 2019

(65) Prior Publication Data

US 2020/0289366 A1 Sep. 17, 2020

(51) Int. Cl.
*A61H 23/02* (2006.01)
*A61M 35/00* (2006.01)
(Continued)

(52) U.S. Cl.
CPC .......... *A61H 23/0254* (2013.01); *A61K 36/00* (2013.01); *A61K 38/1808* (2013.01);
(Continued)

(58) Field of Classification Search
CPC .......... A61H 7/00; A61H 7/001; A61H 7/002; A61H 7/003; A61H 7/004; A61H 7/005; A61H 15/00; A61H 15/0078; A61H 15/0085; A61H 15/0092; A61H 15/02; A61H 2015/0071; A61H 23/00; A61H 23/02; A61H 23/0254; A61H 2201/0157; A61H 2201/10; A61H 2201/105; A61H 2201/12; A61H 2201/1207; A61H 2201/5015; A61H 2205/022;
(Continued)

(56) References Cited

U.S. PATENT DOCUMENTS 3,661,018 A * 5/1972 Keefer ................. A46B 13/023
                                                15/22.1
4,115,893 A * 9/1978 Nakata .................. A46B 3/005
                                                15/110
(Continued)

*Primary Examiner* — Justine R Yu
*Assistant Examiner* — Matthew D Ziegler
(74) *Attorney, Agent, or Firm* — Mark C. Johnson; Johnson Dalal

(57) ABSTRACT

A lip augmentation assembly and method of selectively plumping the lips provides a housing having a first end forming a grip, and a second end. The housing encases a motor and a vibrating member. A vibrating head snugly couples to the second end of the housing. The head engages the inner surface of the lips. The head has an irregular oval shape, opposing wide sidewalls, opposing narrow sidewalls, and a concave-shaped terminus. Vibration nodules are arranged in a grid-like pattern on the wide and narrow sidewalls of the head. The vibration nodules receive vibrations from the vibrating member. An epidermal cell growth serum is topically applied to the lips before, and after, engagement with the vibration nodules. Pressing the wide sidewall of the head against the inner surface of lips, applies a deeply focused pressure on the lip. Pressing the narrow sidewall against the lips augments selected segments of lips.

16 Claims, 10 Drawing Sheets

(51) Int. Cl.
*A61K 38/18* (2006.01)
*A61K 36/00* (2006.01)

(52) U.S. Cl.
CPC ..... *A61M 35/003* (2013.01); *A61H 2201/105* (2013.01); *A61H 2201/5015* (2013.01); *A61H 2205/022* (2013.01); *A61M 2210/0625* (2013.01)

(58) Field of Classification Search
CPC .............. A61H 2205/026; A61K 36/00; A61K 38/1808; A61M 35/00; A61M 35/003; A61M 2210/0625; A45D 34/04–048
See application file for complete search history.

(56) References Cited

U.S. PATENT DOCUMENTS

| | | | |
|---|---|---|---|
| 4,205,664 A * | 6/1980 | Baccialon | A61H 13/00 601/141 |
| 4,827,551 A * | 5/1989 | Maser | A61H 13/00 15/24 |
| 4,846,158 A * | 7/1989 | Teranishi | A61H 23/0263 601/72 |
| 4,858,600 A * | 8/1989 | Gross | A61H 15/0085 601/159 |
| 5,117,815 A * | 6/1992 | Gentry | A61H 23/0263 601/138 |
| 6,139,553 A | 10/2000 | Dotan | |
| 7,273,327 B2 * | 9/2007 | Hohlbein | A46B 15/0081 401/132 |
| 7,654,271 B2 * | 2/2010 | Wyatt | A45D 40/265 132/218 |
| 8,048,089 B2 | 11/2011 | Ignon et al. | |
| 8,177,450 B2 | 5/2012 | Zhang | |
| 8,425,134 B2 * | 4/2013 | Gueret | A45D 40/26 401/126 |
| 8,622,952 B2 | 1/2014 | Goldberg et al. | |
| 8,858,472 B2 | 10/2014 | Gomez | |
| 8,945,104 B2 | 2/2015 | Boone, III et al. | |
| 9,119,758 B2 | 9/2015 | Ho | |
| 9,132,058 B2 * | 9/2015 | Imboden | A61H 19/00 |
| D767,153 S | 9/2016 | Infante et al. | |
| 9,597,256 B1 * | 3/2017 | Paul | A61H 23/0263 |
| D819,222 S | 5/2018 | Nelson et al. | |
| 2002/0156403 A1 * | 10/2002 | Meginniss, III | A46B 15/00 601/46 |
| 2003/0165550 A1 * | 9/2003 | Rhoades | A45D 34/041 424/401 |
| 2004/0015139 A1 * | 1/2004 | La Bianco | A61B 17/54 604/289 |
| 2004/0073144 A1 | 4/2004 | Carava | |
| 2004/0260209 A1 | 12/2004 | Ella et al. | |
| 2005/0113725 A1 * | 5/2005 | Masuda | A61H 23/0263 601/72 |
| 2005/0142093 A1 * | 6/2005 | Skover | A61B 17/54 424/70.14 |
| 2006/0058714 A1 * | 3/2006 | Rhoades | A45D 24/007 601/73 |
| 2009/0198159 A1 * | 8/2009 | Linzell | A61H 7/003 601/138 |
| 2009/0306577 A1 | 12/2009 | Akridge et al. | |
| 2010/0222719 A1 | 9/2010 | Cowie et al. | |
| 2013/0041211 A1 | 2/2013 | Zamar | |
| 2013/0110014 A1 | 5/2013 | Luzon et al. | |
| 2013/0123675 A1 * | 5/2013 | Oki | A61H 13/00 601/112 |
| 2014/0058300 A1 * | 2/2014 | Ungemach | A61H 7/005 601/136 |
| 2014/0128780 A1 | 5/2014 | Kennedy et al. | |
| 2015/0141884 A1 * | 5/2015 | Thiebaut | A61H 7/00 601/112 |
| 2015/0342825 A1 | 12/2015 | Shabazian et al. | |
| 2016/0008215 A1 * | 1/2016 | Pfeiffer | A61H 23/02 600/38 |
| 2016/0045081 A1 * | 2/2016 | Kern | A47K 7/043 15/22.4 |
| 2017/0036002 A1 * | 2/2017 | Ignon | A61N 5/0617 |
| 2017/0172837 A1 * | 6/2017 | Yang | A61H 7/005 |
| 2018/0185235 A1 * | 7/2018 | Nelson | A61H 7/008 |
| 2019/0142691 A1 * | 5/2019 | Sedic | A61H 23/02 |

* cited by examiner

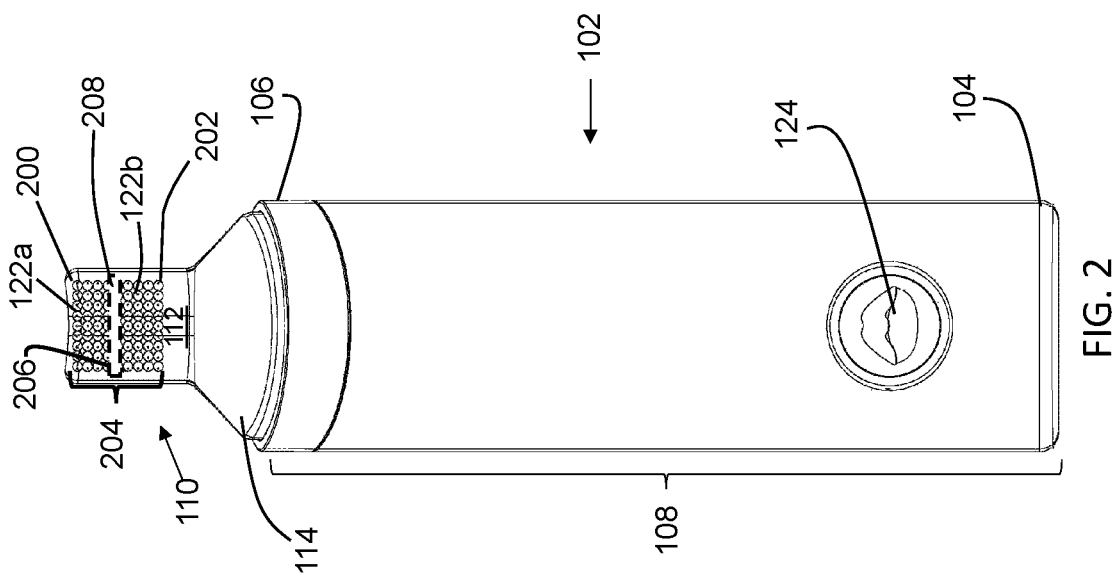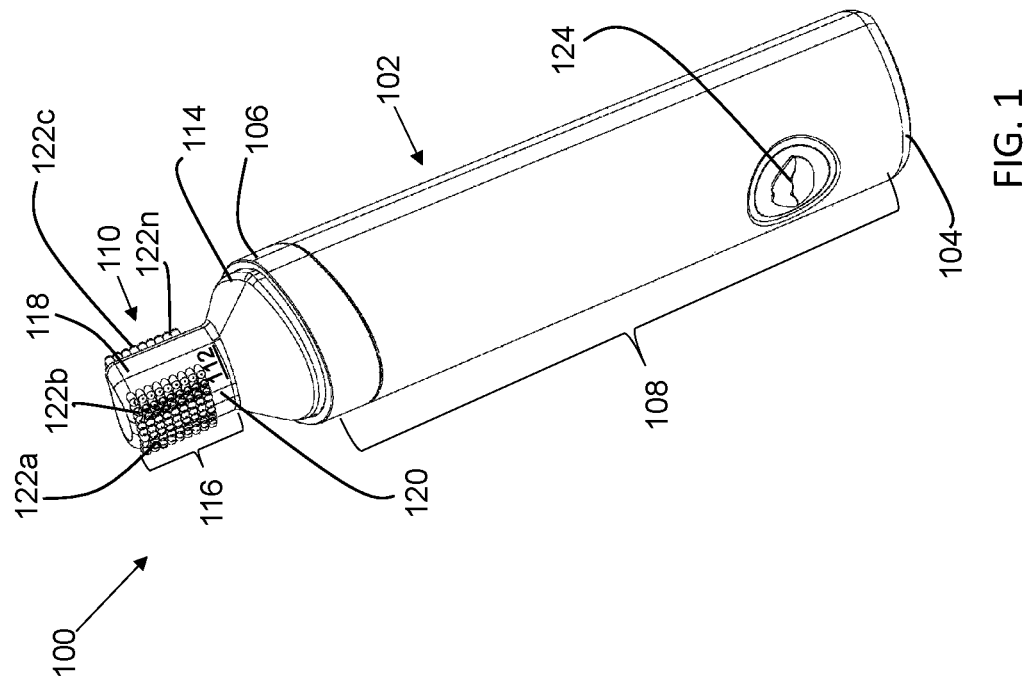

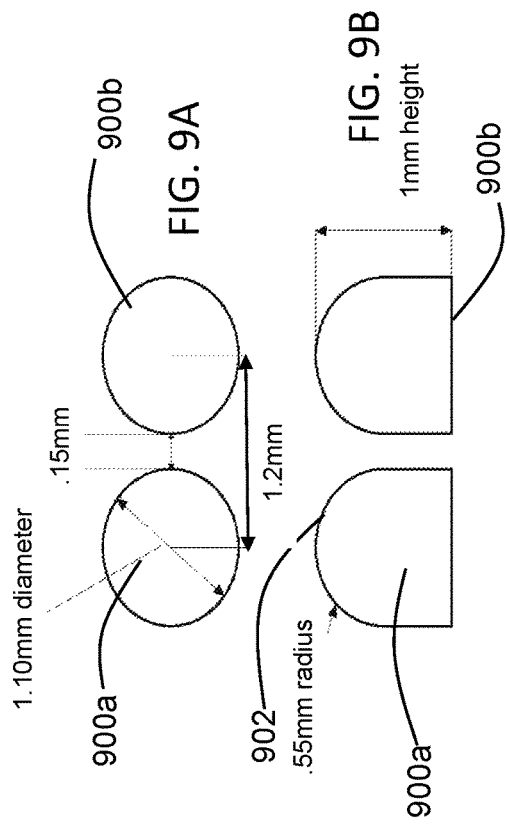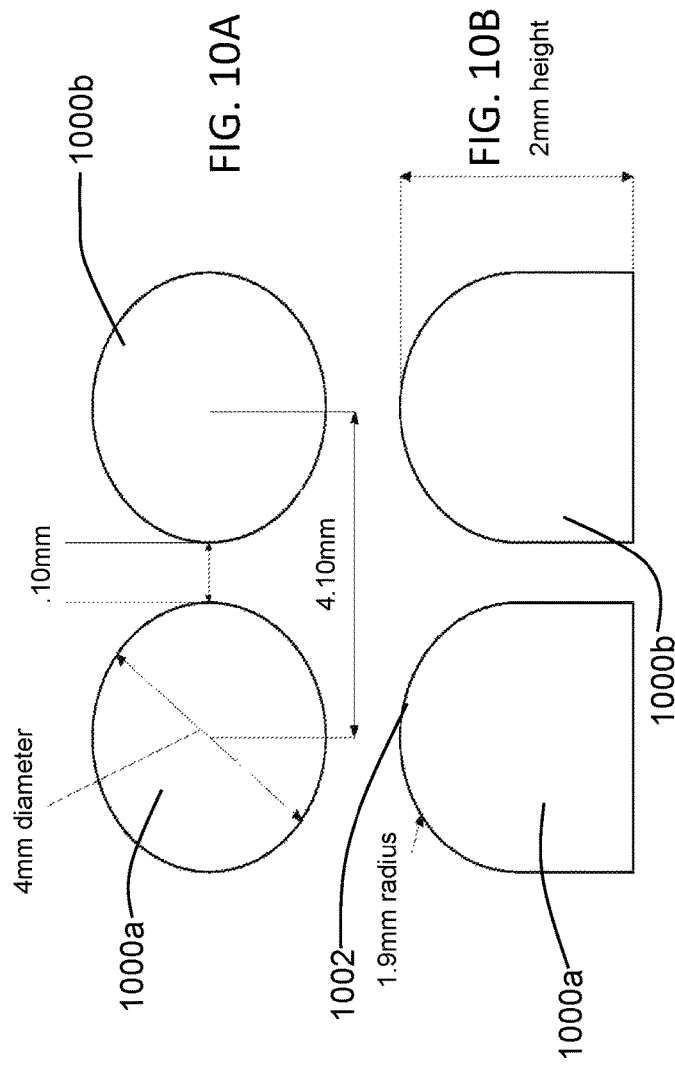

LIP AUGMENTATION ASSEMBLY AND METHOD OF SELECTIVELY PLUMPING SEGMENTS OF THE LIPS

FIELD OF THE INVENTION

The present invention relates generally to a lip augmentation assembly and method of selectively plumping segments of the lips to alter the appearance of all, or selected segments, of the lips by increasing their fullness.

BACKGROUND OF THE INVENTION

Many known lip augmentation devices designed to create micro trauma in a user's lips fail to efficiently effectuate the same. Specifically, some known devices are not handheld and/or are arduous to handle or manipulate. Additionally, the application surface (or part of the augmentation device designed to contact a user's lips) does not provide adequate or sufficient coverage on a user's lips, requiring the user of the device to use it for longer than many users desire. Additionally, the application surface or configuration thereof is not conducive to receiving an adequate or sufficient portion of a user's lips. Further, many known devices do not utilize creams or other liquids to enhance the lip-augmentation process.

Other proposed solutions or devices to augment a user's lips, including those which may utilize enhancement creams, liquids, or gels, alter a limited number of segments or portions of a user's lips. Also, those known lip augmentation methods and devices do not activate cell regeneration deep within the lip. Also, they do not provide a plurality of tightly-spaced, grid-shaped vibration nodules covering a portion of the head that dig deeply approximately 1 millimeter deep into the lip mucosa to create harmless micro trauma without actually puncturing the mucosa, thereby activating cell regeneration deeply within the mucosa, as opposed to only on the surface.

Even though the above-referenced devices, creams, and methods for augmenting a user's lips meet some of the needs of the market, a lip augmentation assembly and method of selectively plumping segments of a user's lips that provides a vibrating head that engages the inner surface of the lips while vibrating, and which has an irregular oval shape defined by opposing wide sidewalls for engaging the entire inner surface of the lips, opposing narrow sidewalls for selective engagement of segments of the lips, and a plurality of vibration nodules arranged in a grid-shaped pattern; whereby the lips are coated with an epidermal cell growth serum for topical application of an epidermal cell growth serum to the lips by the vibrating vibration nodule, is still desired. Therefore, a need exists to overcome the problems with the prior art as discussed above.

SUMMARY OF THE INVENTION

The invention provides a lip augmentation assembly and method of selectively plumping segments of the lips that overcome the hereinafore-mentioned disadvantages of the heretofore-known devices and methods of this general type and that alters the appearance of all, or selected segments, of the lips by increasing their fullness.

With the foregoing and other objects in view, there is provided, in accordance with the invention, a lip augmentation assembly that provides a vibrating head configured to snugly engage the inner surface of the lips, or lip mucosa, while vibrating and topically applying and embedding an epidermal cell growth serum on the lips. The head is covered with rigid vibration nodules that dig into the inner surface of the lip while vibrating. The head is defined by opposing wide sidewalls that engage the entirety of the lips, and opposing narrow sidewalls that enable selective engagement of segments of the lips. The combination of deep mechanical vibrations, and epidermal cell growth serum works to alter the appearance of all, or selected segments, of the lips by increasing their fullness.

In some embodiments, the assembly may include a housing that is defined by a first end forming a grip, and a second end. A housing length separates the first and second ends of the housing. The assembly further comprises a vibrating head that is configured to detachably couple to the second end of the housing, while being manipulated to press against the inner surface of the lips.

The head is defined by an irregular oval shape having an outer surface. The outer surface includes opposing wide sidewalls, opposing narrow sidewalls, and a concave-shaped terminus. The wide sidewalls are configured to engage the entire inner surface of the lips while vibrating. The narrow sidewalls are configured to selectively engage segments of the lips while vibrating. The concave-shaped terminus contours to the lips and interior portion of the mouth for enhanced comfort.

An upper side of the head spans a width of the head from the second end of the housing to an upper-side termination point. A bottom side, opposing the upper side of the head, spans the width of the head from the second end of the housing to a bottom-side termination point. The lower end is disposed opposite the second end of the housing, and has a head length separating the lower end of the head and the second end of the housing. The upper-side termination point and the bottom-side termination point are both disposed along the head length a distance greater than 50% the head length.

The housing encapsulates an electric motor that is operationally connected to the head, and having a vibrating member surrounded by the head and operably coupled to an activation button. The electric motor actuates the vibratory motion of the head.

A plurality of vibration nodules are arranged in a grid-shaped pattern on both the wide sidewalls and narrow sidewalls of the head. The vibration nodules are configured to receive a plurality of vibrations from the vibrating member. The vibration nodules are rigid and tightly-spaced, such that pressing the vibrating head against the inner surface of the lips, applies a deeply focused pressure and mechanical vibration on the lips.

An epidermal cell growth serum is topically applied to the lips. The vibration nodules topically apply the epidermal cell growth serum to the inner surface of the lips while vibrating. The vibration by the vibration nodules works to indent the epidermal cell growth serum into the lips for simultaneous blood circulation and dispensing of the serum to the lips. The vibration nodules dig into the inner surface of the lip to create harmless micro trauma without actually puncturing the lip. This results in activating cell regeneration deeply within the lip.

The housing also encapsulates a power source, an activation button, a USB port, and a circuit board to regulate aspects of the vibratory motion. Further, an outer case encapsulates the housing. The outer case forms a charge opening and a switch opening that enables access to the USB port and the activation button, respectively.

In accordance with another feature, an embodiment of the present invention plies an epidermal cell growth serum to the inner surface of the lips with the vibration nodules.

In accordance with a further feature of the present invention, the upper-side termination point and the bottom-side termination point are aligned with one another.

In accordance with a further feature of the present invention, the head further comprises a lower end opposite the second end of the housing and a head length separating the lower end of the head and the second end of the housing, the upper-side termination point and the bottom-side termination point both disposed along the head length a distance greater than 50% the head length.

In accordance with a further feature of the present invention, a nodule application length separates the second end of the housing and the upper-side termination point and the bottom-side termination point, respectively and defining a nodule application length midpoint and with a first nodule plane spanning through the nodule application length midpoint, wherein the plurality of vibration nodules are symmetrically disposed with respect to one another about the first nodule plane.

In accordance with a further feature of the present invention, the plurality of vibration nodules are symmetrically disposed with respect to the midpoint of the width of the head.

In accordance with a further feature of the present invention, the housing is bifurcated into a top piece and a bottom piece.

In accordance with a further feature of the present invention, the housing is fabricated from Acrylonitrile Butadiene Styrene.

In accordance with a further feature of the present invention, the epidermal cell growth serum includes at least one of the following: a plant stem cell, a growth factor, an epidermal growth factor, and a basic fibroblast growth factor.

In accordance with a further feature of the present invention, the head is defined by a mouth that forms a snap-fit relationship with the second end of the housing.

In accordance with a further feature of the present invention, the head is fabricated from Acrylonitrile Butadiene Styrene rated by the Food and Drug Administration.

In accordance with a further feature of the present invention, the wide sidewalls of the head are generally flat.

In accordance with a further feature of the present invention, the wide sidewalls of the head have a width of about 21.30 millimeters.

In accordance with a further feature of the present invention, the narrow sidewalls of the head are generally rounded.

In accordance with a further feature of the present invention, the narrow sidewalls of the head have a width of about 16.36 millimeters.

In accordance with a further feature of the present invention, the irregular oval shape of the head has a radius of about 9.50 millimeters.

In accordance with a further feature of the present invention, the concave-shaped terminus of the head has a radius of about 44.75 millimeters.

In accordance with a further feature of the present invention, the length of the head is about 18.5 millimeters.

In accordance with a further feature of the present invention, the vibration nodules are spaced apart about 0.1 to 0.2 millimeters from each other.

In accordance with a further feature of the present invention, the vibration nodules have a height of about 1 to 2 millimeters.

In accordance with a further feature of the present invention, the vibration nodules have a diameter of about 1.1 to 4 millimeters.

In accordance with a further feature of the present invention, the vibration nodules per centimeter squared are about 6 to 64.

In accordance with a further feature of the present invention, the head produces a mechanical vibration of about 2500-10000 rotations per minute.

In accordance with a further feature of the present invention, the power source comprises a battery have a volt range between 1.5 Volts Direct Current to 8 Volts Direct Current.

In accordance with a further feature of the present invention, the circuit board has a load current between about 0.2 amps to 0.8 amps.

In accordance with a further feature of the present invention, the assembly further comprises a lighted switch cover overlaying the activation button.

In accordance with a further feature of the present invention, the outer case is fabricated from casted 6061 aluminum.

In accordance with the present invention, a method of selectively plumping segments of the lips. The method includes an initial Step of aligning a lip augmentation assembly with the lips, the lip augmentation assembly comprising a head, the head being defined by opposing wide sidewalls being covered by a plurality of vibration nodules, opposing narrow sidewalls being covered by the vibration nodules, and a concave-shaped terminus.

The method 200 may further comprise a Step of applying an epidermal cell growth serum on an inner surface of the lips.

A Step includes triggering vibrations through the head, whereby the vibration nodules uniformly vibrating between about 2500 to 10000 rotations per minute.

In some embodiments, a Step comprises engaging the inner surface of the lips with the vibration nodules covering the wide sidewalls, whereby the vibrations are administered in a perpendicular orientation to the inner surface of the lips.

A Step includes engaging a portion of the lips with the vibration nodules covering the narrow sidewalls, whereby the vibrations are administered in a perpendicular orientation to the selected portion of the lips.

In some embodiments, a Step may include applying pressure on the head on the head while the vibration nodules engage the lips for a duration between 60 to 300 seconds, whereby the epidermal cell growth serum is topically applied to the lips.

A Step comprises reapplying the epidermal cell growth serum on the inner surface of the lips.

A final Step includes repeating the vibratory application of epidermal cell growth serum with the lip augmentation assembly at least every other day.

One objective of the present invention is to alter the appearance of all, or selected segments, of the lips by increasing their fullness.

Another objective is to utilize vibration to create uniform augmentation of the lips, or selected portions of the lips.

Another objective is to enable a plurality of vibration nodules to receive a plurality of vibrations from the vibrating member between about 2500 to 10000 rotations per minute.

Another objective is to activate cell regeneration deep within the lip.

Another objective is to incorporate an epidermal cell growth serum on the lips prior to, and immediately after engaging the lips with the vibratory motion of the vibration nodules.

Another objective is to provide a plurality of tightly-spaced, grid-shaped vibration nodules covering a portion of the head that dig deeply approximately 1 millimeter deep into the lip mucosa to create harmless micro trauma without actually puncturing the mucosa, thereby activating cell regeneration deeply within the mucosa, as opposed to only on the surface.

Another objective is to provide deeply focused pressure and mechanical vibration on the lip mucosa, so as to increase the overall volume of the lips by targeting a deeper portion of the mucosa and making it thicker through new cell growth and enhance collagen production Another objective is to form a uniform augmentation of the lips.

Another objective is to plump the entire lips by engaging the inner surface of the lips with the vibration nodules covering the wide sidewalls.

Another objective is to plump selected segments of the lips by engaging the inner surface of the lips with the vibration nodules covering the narrow sidewalls.

Another objective is to provide an easy to use lip augmentation assembly and method of selectively plumping segments of the lips.

Another objective is to provide an inexpensive to manufacture lip augmentation assembly.

Although the invention is illustrated and described herein as embodied in a Lip Augmentation Assembly and Method of Selectively Plumping Segments of the Lips, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the housing.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 1 is a perspective view of an exemplary lip augmenting assembly, in accordance with an embodiment of the present invention;

FIG. 2 is an elevated side view of the lip augmenting assembly shown in FIG. 1, in accordance with an embodiment of the present invention;

FIGS. 9A and 9B are views of a small vibration nodule, where FIG. 9A is a side view, and FIG. 9B is a top view, in accordance with an embodiment of the present invention;

FIGS. 10A and 10B are views of a large vibration nodule, where FIG. 10A is a side view, and FIG. 10B is a top view, in accordance with an embodiment of the present invention;

DETAILED DESCRIPTION

Figure 4:
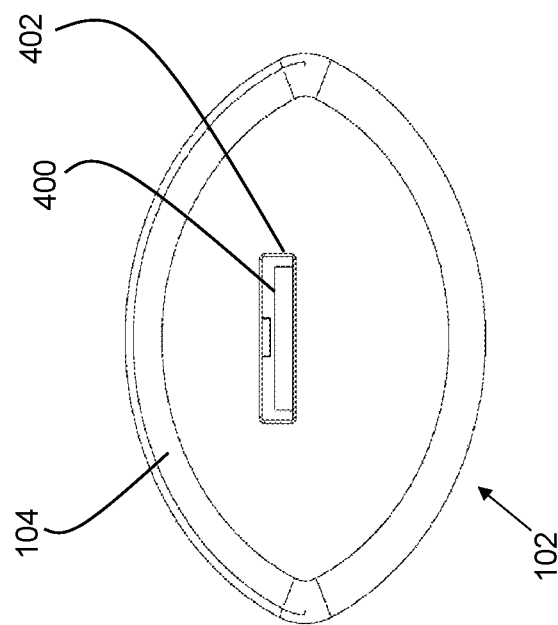
FIG. 4 is a bottom view of the lip augmenting assembly shown in FIG. 1, in accordance with an embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient lip augmentation assembly and method of selectively plumping segments of the lips. Embodiments of the invention provide a lip augmentation assembly 100 that provides a vibrating head 110 configured to snugly engage the inner surface 1202 of a user's lips or, more specifically, the lip mucosa, while vibrating and topically applying and embedding an epidermal cell growth serum 1204 on the lips 1200. The head 110 is covered with substantially rigid vibration nodules 122a-n, wherein "n" represents any number greater than 1. The vibration nodules 122a-n dig into the inner surface of the user's lip while vibrating. The head 110 is defined by opposing wide sidewalls 302a, 302b that engage the entirety of a user's lips, and opposing narrow sidewalls that enable selective engagement of segments of the lips 1200. The combination of deep mechanical vibrations, and epidermal cell growth serum 1204 works to alter the appearance of all, or selected segments, of the lips 1200 by increasing their fullness.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components.

The first example of a lip augmentation assembly 100, as shown in FIG. 1, includes a housing 102 that couples to a vibrating head 110. The head 110 is configured, shaped, and sized to fit into the mouth and vibrate against the inner surface 1202 of the lips. The head 110 is also configured to engage the inner surface 1202 of the lips with vibration nodules 122a-n substantially covering ("covering") the vibrating head 110, while simultaneously topically applying an epidermal cell growth serum 1204 on the lips, both before and after engagement with the vibrating head 110. The inner surface 1202 of the lips may include, without limitation, the labial mucosa.

The lip augmentation assembly 100 is also unique in using a vibrating head 110 defined by an irregular oval shape having opposed substantially flat and wide sidewalls 302a-b. The head 110 may also include opposed rounded and narrow sidewalls 304a-b. The wide sidewalls 302a, 302b fully engages the entirety of the lips 1200 for full lip augmentation. The narrow sidewalls 304a, 304b may have a lesser profile, enable selective engagement with segments of the lips 1200.

As FIG. 1 references, the lip augmentation assembly 100, hereafter "assembly 100" comprises a housing 102 that is defined by a first end 104, a second end 106, and a housing length 108 that separates the first and second ends 104, 106. The first end 104 of the housing 102 provides a grip for manipulation of the assembly 100. The second end 106 of the housing 102 couples to a vibrating head 110 covered with a plurality of vibration nodules 122a-n. An activation button 124 is disposed thereon along the housing length 108 to actuate vibrations through the vibration nodules 122a-n, as described below.

In one embodiment, the housing 102 is bifurcated into a top piece 1114 and a bottom piece 1116 that fasten together through screw, adhesives, or a snap-fit relationship. The housing 102 may be configured to have a generally elongated, cylindrical shape. Though in other embodiments, the housing 102 may be rectangular, circular, triangular, square, or irregular-shaped. The shapes and dimensions of the housing 102 enable facilitated gripping and manipulating of the assembly 100. This allows a user to grip the first end 104 of the housing 102 while pressing and manipulating the vibrating head 110 against the lips 1200, and specifically the inner surface 1202 of the lips. The housing 102 also contains electrical components for actuating the vibrations, and ports for accessing the activation button 124 and receiving electrical charges (FIG. 4). In some embodiments, the housing 102 may be fabricated from Acrylonitrile Butadiene Styrene or a rigid polymer.

Figure 3:
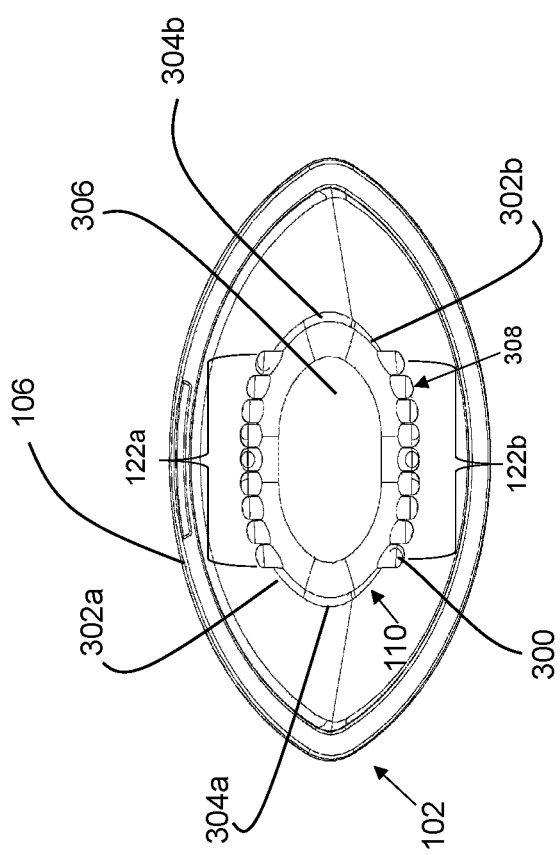
FIG. 3 is a top view of the lip augmenting assembly shown in FIG. 1, in accordance with an embodiment of the present invention.

As FIG. 3 illustrates, the assembly 100 further comprises a head 110 that joins with the second end 106 of the housing 102. The head 110 is operably attached to the housing 102. In particular, the head 110 can be temporarily attached to the housing 102, when operational to engage the lips 1200. Alternatively, the head 110 can also be temporarily detached from the housing 102, when the head 110 is not disposed for use, or when requiring external or internal repair.

Figure 5:
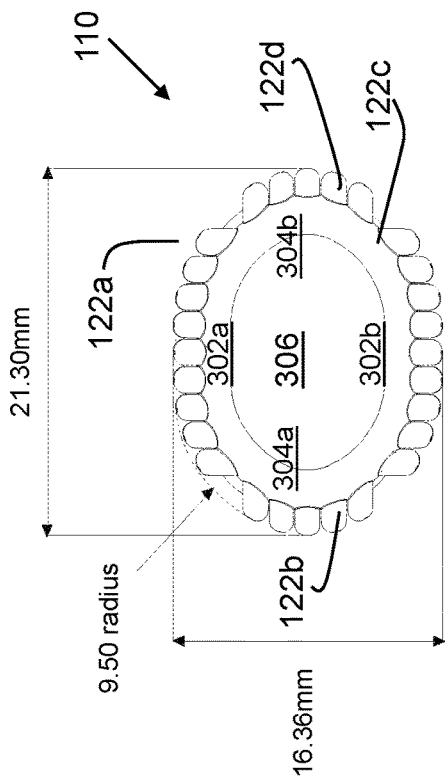
FIG. 5 is a top view of the vibration nodules, in accordance with an embodiment of the present invention.

The head 110 is defined by an irregular oval shape having an outer surface 112. Though in other embodiments, the head 110 may have a generally cylindrical, or circular shape. In one non-limiting embodiment, the irregular oval shape of the head 110 has a radius of about 9.50 millimeters (FIG. 5). Though other radiuses may be used, depending on the shape of the head 110. The head 110 is sized and dimensioned to engage the inside surface 1202 of the lips, as the lips wrap around the head 110. In one exemplary use of the head 110, the head 110 engages the lips for 30-300 seconds while vibrating. In one non-limiting embodiment, the head 110 is fabricated from Acrylonitrile Butadiene Styrene rated by the Food and Drug Administration.

Further, the head 110 is used in conjunction with a specially formulated epidermal cell growth serum 1204 that further enhances augmentation of the lips 1200. This combination of serum 1204 and vibratory motion to extrude the serum 1204 deep into the lips works to increase blood flow to the lips and nitric oxide production in the lip tissue; thereby causing an immediate increase in lip volume.

As shown in FIG. 5, the outer surface 112 of the head 110 includes opposing wide sidewalls 302a, 302b, opposing narrow sidewalls 304a, 304b, and a concave-shaped terminus 306. The wide sidewalls 302a, 302b are configured to engage the entire inner surface 1202 of the lips while vibrating. In one non-limiting embodiment, the wide sidewalls 302a, 302b of the head 110 are generally flat and have a width of about 21.30 millimeters.

The narrow sidewalls 304a, 304b are configured to selectively engage segments of the lips while vibrating. The concave-shaped terminus 306 contours to the lips and interior portion of the mouth for enhanced comfort. In one non-limiting embodiment, the narrow sidewalls 304a, 304b of the head 110 are generally rounded and have a width of about 16.36 millimeters.

In another non-limiting embodiment, the concave-shaped terminus 306 of the head 110 has a radius of about 44.75 millimeters. In some embodiments, the substantially concave configuration of the concave-shaped terminus 306 may resemble an outline or surface that curves inward like the interior of a circle or sphere in relation to the lips. The substantially concave configuration is structured to allow the user to effortlessly engage the lips with the vibrating head 110 during the lip augmentation process.

As a result, at least a portion of the lips 1200 can contour within the dimensions of the head 110. The concave configuration of the concave-shaped terminus 306 further ensures that the lips 1200 are uniformly augmented throughout the lip augmentation procedure. In addition, the substantially concave shape of the concave-shaped terminus 306 is not limiting, which allows for uniform augmentation of any portion of the lips 1200. The concave shape of the concave-shaped terminus 306 can also help prevent any structural damages to the lips 1200, ensuring that the lip augmentation is safe, consistent, and uniform.

Turning back to the illustrations of the head 110 in FIGS. 1-3, the head 110 includes a lower end structure 114 with a bottom end 126 that is disposed opposite the first end 104 of the housing 102 and an upper end 128 terminating where a head length 116 begins and where the plurality of vibration nodules 122a-n are disposed. The lower end 114 of the head 110 may form a mouth that forms a snap-fit relationship with the second end 106 of the housing 102 to enable coupling and decoupling thereto. The lower end 114 separates the head length 116 from the second end 106 of the housing 102. The head length 116 can be seen separating the terminal end 128 of the lower end structure 114 of the head 110 and the terminus 306 of the head 110. The lower end structure 114 of the head 110 can be seen tapering in width from the bottom end 126 of the lower end structure 114 to the upper end 128 of the lower end structure 114 of the head 110, whereby the width of the wide sidewalls 302a, 302b can be seen being less than the width of the bottom end 126 of the lower end structure 114 proximal to the second end 106 of the housing 102. In one non-limiting embodiment, the head length 116 is about 18.5 millimeters. Though in other embodiments, other lengths may be used.

In some embodiments, the head 110 has an upper side 118 that spans a width of the head 110 from the second end 106 of the housing 102 to an upper-side termination point 200. The head 110 also has a bottom side 120 that opposes the upper side 118. The bottom side 120 of the head 110 spans the width of the head 110 from the second end 106 of the housing 102 to a bottom-side termination point 202.

In one non-limiting embodiment, the upper-side termination point 200 and the bottom-side termination point 202 are aligned with one another. This alignment along the head length 116 creates a symmetrical configuration for the head 110, which enhances balance and vibrations of the head 110 during lip augmentation. In another embodiment, the upper-side termination point 200 and the bottom-side termination point 202 of the head are both disposed along the head length 116 at a distance greater than 50% the head length 116. This creates greater space for vibration nodules 122a-n.

The height of the head 110 can range from approximately 10 mm to 30 mm with the ideal height being about 18.5 mm. The wide sidewalls 302a, 302b of the head 110 can range from 10 mm to 30 mm with the ideal size being 21.3 mm. The narrow sidewalls 304a, 304b of the head 110 can range from 8 mm to 25 mm with the ideal size of 16.36 mm.

Figure 13:
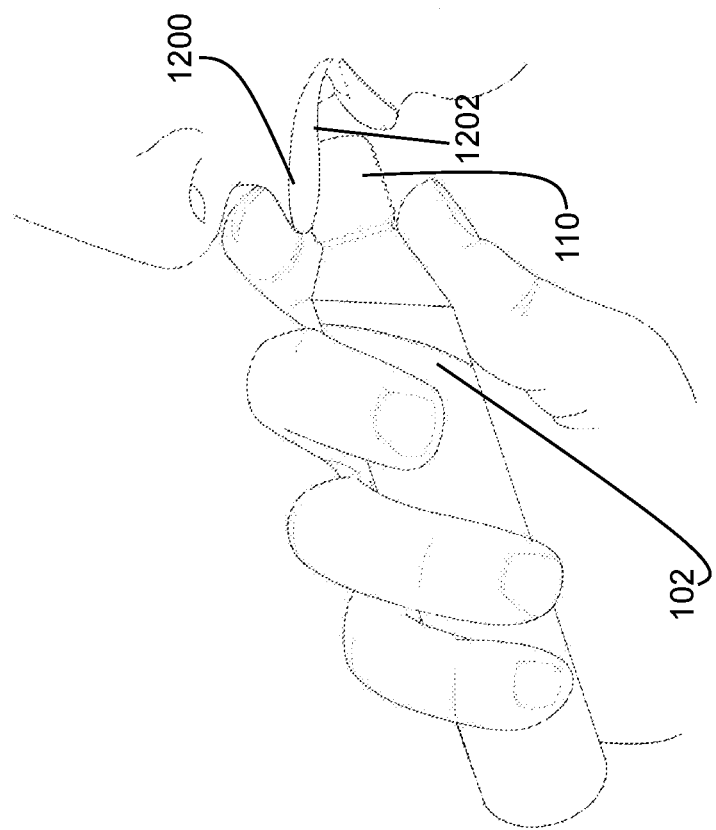
FIG. 13 is a perspective side view of the lip augmenting assembly augmenting an upper lip, showing the vibrating head pressing against the inner surface of the upper lip, in accordance with an embodiment of the present invention.
Figure 12:
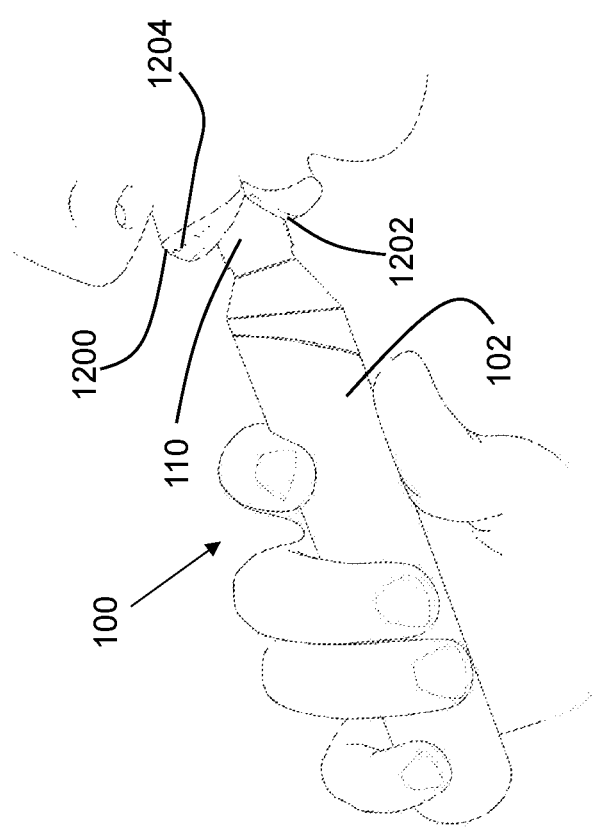
FIG. 12 is a perspective side view of the lip augmenting assembly augmenting the lips, showing the vibrating head fully inserted into the mouth and pressing against the inner surface of the lips, in accordance with an embodiment of the present invention.
Figure 14:
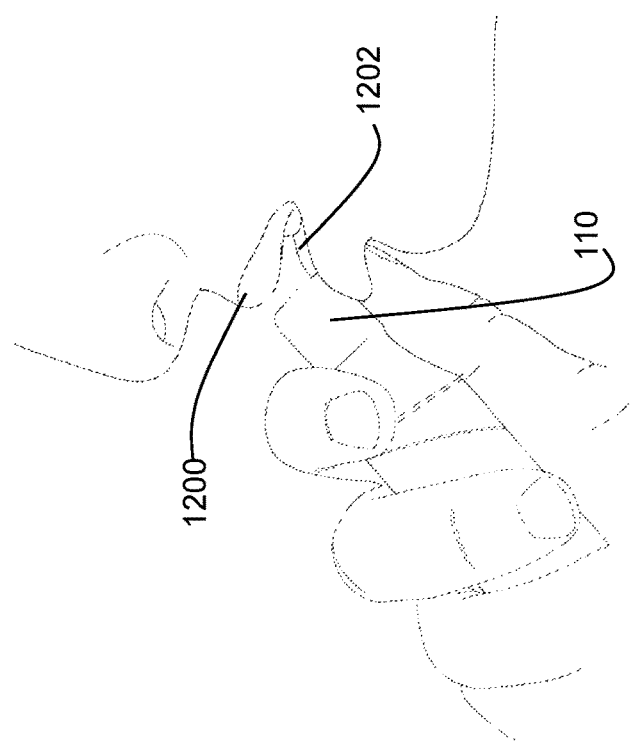
FIG. 14 is a perspective side view of the lip augmenting assembly augmenting a lower lip, showing the vibrating head pressing against the inner surface of the lower lip, in accordance with an embodiment of the present invention.

In one possible embodiment, the shape of the head 110 is an imperfect, or irregular oval, where the wide sidewalls 302a, 302b of the oval are flat to be able to cover the most area when augmenting the entire bottom and top lip, while the narrow sidewalls 304a, 304b of the oval are curved to be able to focus the vibration on a specific portion of the lip. The unique size and dimensions of the head 110 enable a natural fit into the mouth; and specifically for pressing and manipulating against the inner surface 1202 of the lips 1200. This creates a uniform augmentation of the upper and bottom lips when the user puckers the lips 1200 around the head 110 (FIGS. 12-14).

For example, by engaging the lips with the narrow sidewall of the head 110, a segment of the lips may be augmented (FIGS. 15-17); while the remaining portion of the lips are not augmented. Quite differently, the wide sidewall of the head 110 fully engages the entirety of the lips 1200 for full lip augmentation, as illustrated in FIGS. 12-14.

Figure 11:
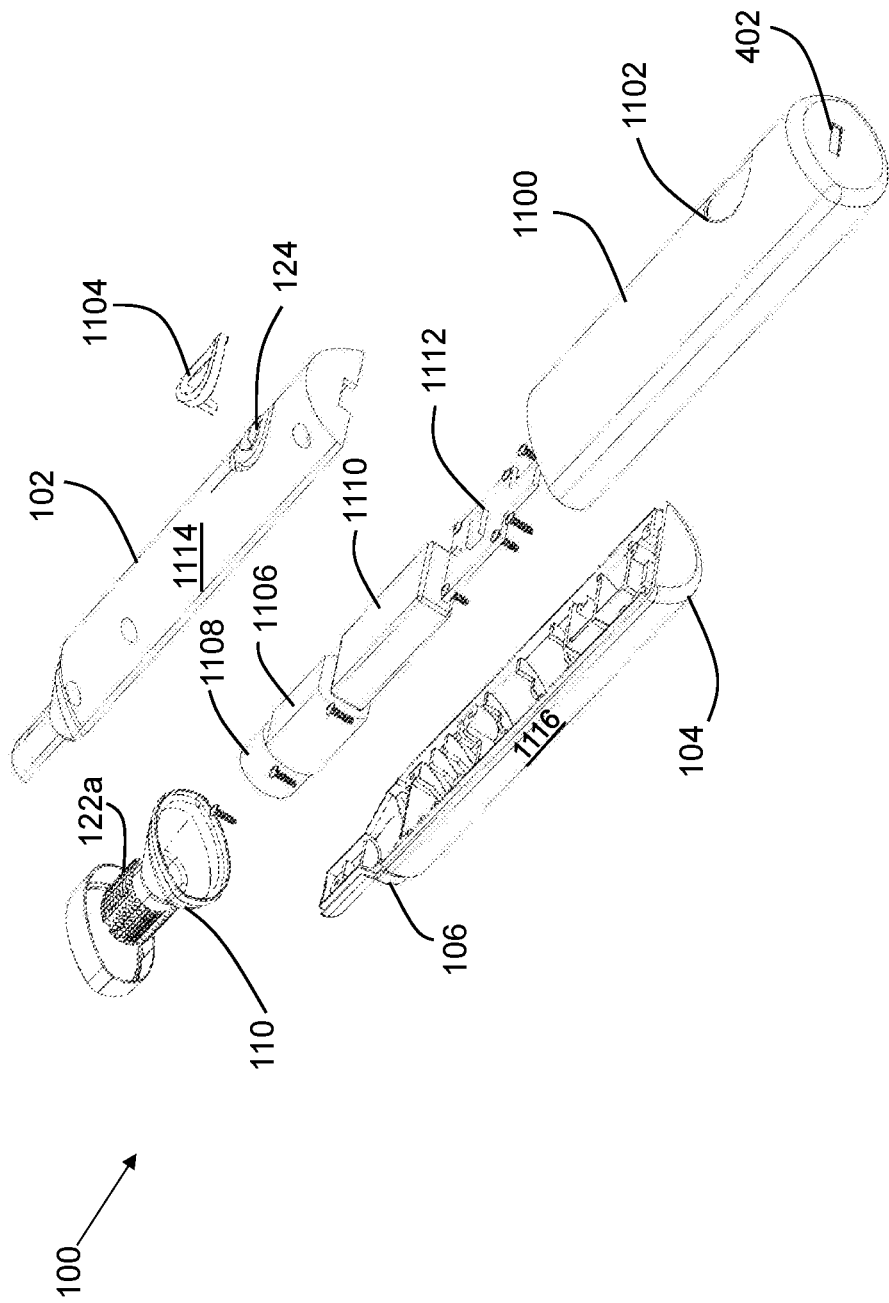
FIG. 11 is an exploded view of the lip augmenting assembly shown in FIG. 1, showing the electrical components inside the housing, and openings forming in the outer casing, in accordance with an embodiment of the present invention.

As FIG. 11 illustrates, the housing 102 encapsulates an electric motor 1106 that is operationally connected to the head 110. A vibrating member 1108 is operationally coupled to the electric motor 1106. The vibrating member 1108 is surrounded by the head 110 and is operably coupled to an activation button 124. The vibrating member 1108 actuates the vibratory motion of the head 110.

The vibrating member 1108 can be a vibrating motor 1106 or similar structures for supplying a plurality of vibrations within a range of frequency and amplitude. In one non-limiting embodiment, the vibrating member 1108 produces a mechanical vibration in the head 110 of about 2500-10000 rotations per minute. The vibrating member 1108 is attached to a power source 1110. The vibrating member 1108 may include other structural features to provide the vibrations, including its circuitry.

Figure 6:
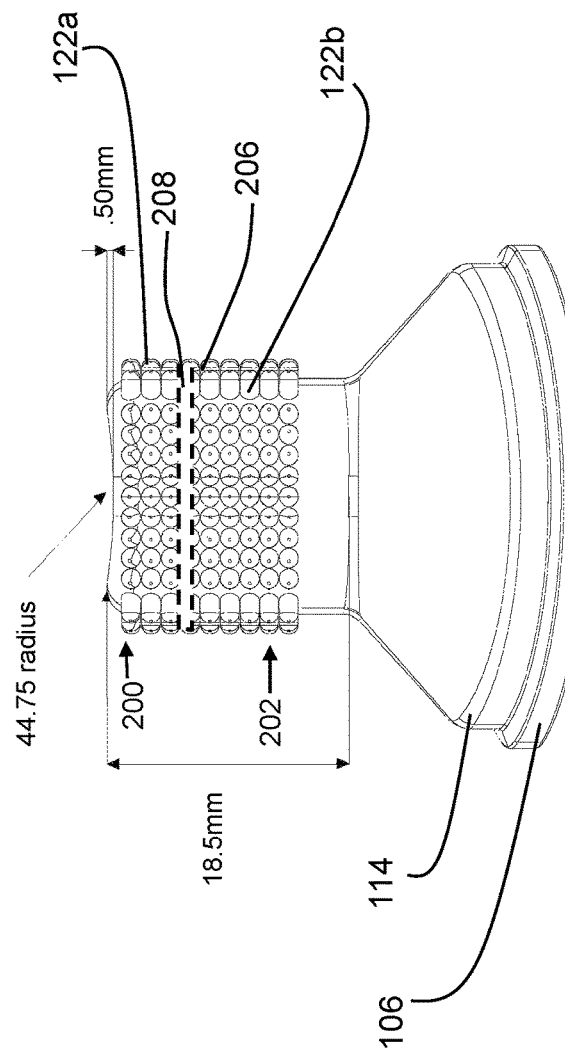
FIG. 6 is an elevated side view of the vibration nodules on the vibrating head, in accordance with an embodiment of the present invention.

Turning now to FIG. 6, the assembly 100 provides a plurality of vibration nodules 122a-n that are arranged in a grid-shaped pattern on both the wide sidewalls 302a, 302b and narrow sidewalls 304a, 304b of the head 110. In one embodiment, the structure of the vibrating head 110 is covered with a plurality of vibration nodules 122a-n arranged in a grid-shaped pattern of aligned rows and columns pattern and spaced tightly together. The vibration nodules 122a-n may be fabricated from hard durometer (plastic or hard silicone).

Looking back at FIG. 3, it can be seen that each of the vibration nodules 122a, 122b, 122c, 122d are disposed in a substantially adjacent and parallel relation to each other. The vibration nodules 122a-n are also disposed in a vibrating relation to the head 110. As such, each of the vibration nodules 122a-n receive a plurality of vibrations passing through the head 110 from the vibrating member 1108. Specifically, the vibrating member 1108 supplies a frequency and amplitude of vibrations to each of the vibration nodules 122a-n.

In one non-limiting embodiment, the vibration nodules 122a-n receive a plurality of vibrations from the vibrating member 1108 between 2500 to 10000 rotations per minute. The vibration nodules 122a-n are rigid and tightly-spaced, such that pressing the vibrating head 110 against the inner surface 1202 of the lips, applies a deeply focused pressure and mechanical vibration on the lips 1200.

The plurality of vibrations provided by the vibrating member 1108 may contribute to a uniform augmentation of the lips 1200 by increasing blood flow to the lips 1200. The plurality of vibrations is comprised of a range of frequency and amplitude. In one embodiment, the frequency of the vibrations can be in the range of about 40 Hertz to about 100 Hertz. The frequency range, however, is not limited. The vibrating member 1108 can be configured to provide vibrations in other ranges of frequencies. The frequency ranges may depend on several factors such as time of use, integrity of the user's lips, desired look of the user, etc.

When pressure is applied to the head 110 against the inner surface 1202 of the lips, the vibration nodules 122a-n dig deeply (approximately 1 millimeter deep) into the labial mucosa to create harmless micro trauma without actually puncturing the labial mucosa. This works to activate cell regeneration deeply within the labial mucosa of the lips, as opposed to only on the surface. This deeply focused pressure and mechanical vibration on the labial mucosa increases the overall volume of the lips by targeting a deeper portion of the labial mucosa and making it thicker through new cell growth and enhance collagen production.

The vibration nodules 122a-n provide the vibrations to at least the portion of the lips 1200 in a perpendicular orientation relative to the lips. Specifically, the frequency and amplitude of vibrations are provided by the vibration nodules 122a-n on the head 110. In some embodiments, when contacted and/or engaged with the surface of the lips 1200, the sidewalls 302a-b, 304a-b are aligned and positioned to allow the vibrations from the vibration nodules 122a-n to perpendicularly vibrate the desired portions of the lips 1200. This increases the intensity of vibrations and allows for uniform dispersion of vibrations onto the vibration nodules 122a-n.

It is also significant to note that the perpendicular orientation of the sidewalls 302a-b, 304a-b to the lips 1200 allows the body to induce its own natural production and flow of hyaluronic acid. It is known in the art that hyaluronic acid is highly beneficial, and used as dermal filler in cosmetic lip augmentation procedures. Having a perpendicular orientation, therefore, ensures a natural, long-term, anti-aging, lip plumping effect in addition to the lip augmentation resulting from the lip augmentation assembly 100.

As FIG. 2 referenced, the vibration nodules 122a-n are symmetrically disposed with respect to the midpoint of the width of the head 110. A nodule application length 204 separates the second end 106 of the housing 102 and the upper-side termination point 200 and the bottom-side termination point 202, respectively. The nodule application length 204 is defined by a nodule application length midpoint 206, and has a first nodule plane 208 spanning through the nodule application length midpoint 206. In this manner, the plurality of vibration nodules 122a-n are symmetrically disposed with respect to one another about the first nodule plane 208. This creates a more symmetrical distribution of vibration nodules 122a-n, and a balanced head 110 during vibrations.

Figure 8:
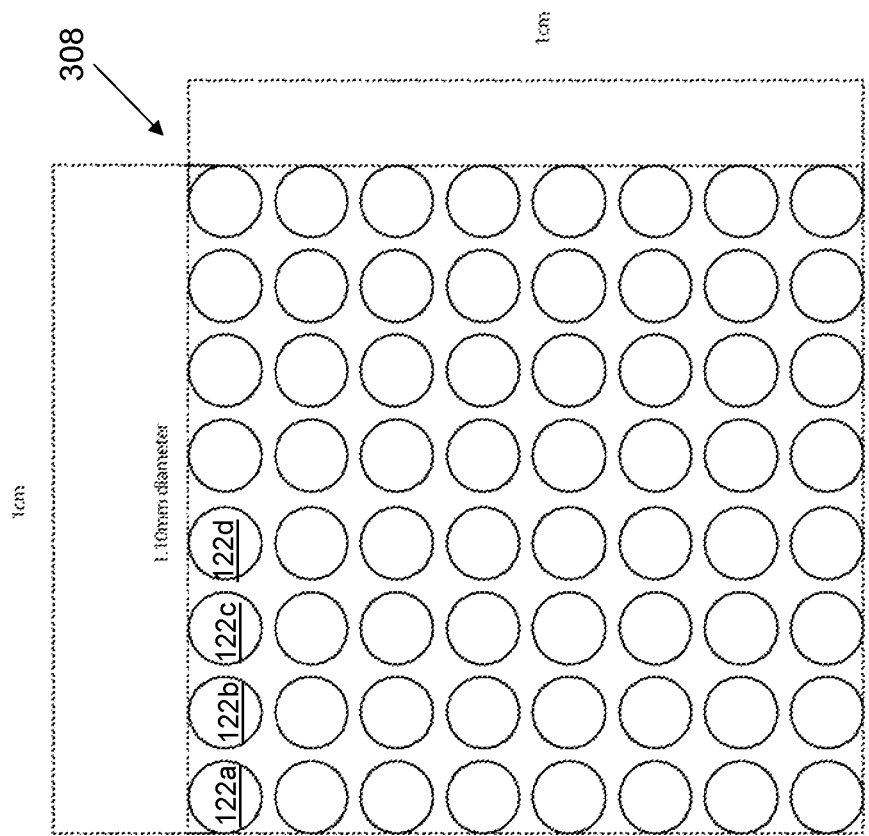
FIG. 8 is a top view of a lip application surface, showing the number of vibration nodules per centimeter squared, in accordance with an embodiment of the present invention.
Figure 7:
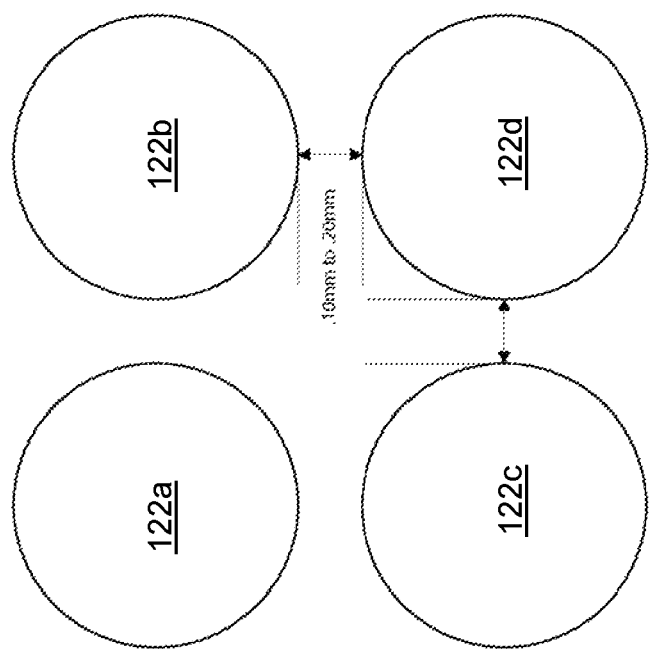
FIG. 7 is a top view of the spacing between the vibration nodules, in accordance with an embodiment of the present invention.

Looking now at FIG. 7, the vibration nodules 122a-n on the head 110 are spaced apart about 0.1 to 0.2 millimeters from each other. Though in other embodiments, different spacing dimensions may be used. In another non-limiting embodiment shown in FIG. 8, there are about 6 to 64 vibration nodules 122a-n per centimeter squared on the lip application surface 308. Though the density of the vibration nodules 122a-n on the lip application surface 308 may be increased or decreased to accommodate different lip augmentation requirements.

In yet another non-limiting embodiment, the vibration nodules 122a-n have a height of about 1 to 2 millimeters, and a diameter of about 1.1 to 4 millimeters. However, in other embodiments, various sizes of vibration nodules 122a-n may be used. For example, FIGS. 9A and 9B show an exemplary small vibration nodule 900a, 900b, where FIG. 9A illustrates 1.10 mm diameter, and 0.15 mm spacing between vibration nodules 900a, 900b. FIG. 9B is a top view of the small vibration nodules, showing a 1 mm height and a 0.55 mm radius for the rounded tip 902.

In another example of larger-sized vibration nodules 122a-n, FIGS. 10A and 10B show views of a large vibration nodules 1000a, 1000b, where FIG. 10A is a side view showing 4 mm diameter, and 0.10 mm spacing between vibration nodules 1000a, 1000b, and FIG. 10B is a top view showing a 2 mm height and a 1.9 mm radius for the rounded tip 1002.

In some embodiments, an epidermal cell growth serum 1204 is topically applied to the lips 1200 prior to, and immediately after engaging the lips with the vibratory motion of the vibration nodules 122a-n (FIG. 12). The active ingredients of the serum 1204 may consist of different combinations of Plant Stem Cells and Epidermal Growth Factor (EGF). In some embodiments, the epidermal cell growth serum 1204 may include, without limitation, a plant stem cell, a growth factor, an epidermal growth factor, and a basic fibroblast growth factor.

The serum 1204 may be applied to the lips 1200 right before engaging the vibration nodules 122a-n across the inner surface 1202 of the lips, as well as immediately after. In addition, the serum 1204 may be applied daily to maintain the desired augmentation results. In yet another embodiment, the epidermal cell growth serum 1204 is applied to the lip mucosa before pressing the vibrating device to the lip mucosa contains ingredients that promote faster proliferation of epidermal cells, such as plant stem cells and/or growth factors such as Epidermal Growth Factor (EGF) and Basic Fibroblast Growth Factor and (BFGF).

The serum 1204 is used to promote faster regeneration and growth of the cells in the lip mucosa after the pressure of the mechanical vibration and the grid-shaped vibration nodules 122a-n create harmless micro trauma to the mucosa which triggers the epidermal cell growth effect and promotes new collagen production. The serum 1204 must be used in combination with the assembly 100, as well as daily to increase the lip augmentation effect of the assembly 100 by promoting cell proliferation of the mucosa of the lips 1200.

As discussed above, the vibration nodules 122a-n work to create uniform augmentation of the lips, or selected portions of the lips. The vibration nodules 122a-n topically apply the epidermal cell growth serum 1204 to the inner surface 1202 of the lips while vibrating. The vibration by the vibration nodules 122a-n works to indent the epidermal cell growth serum 1204 into the lips 1200 for simultaneous blood circulation and dispensing of the serum 1204 to the lips 1200.

Specifically, the vibration nodules 122a-n dig into the inner surface of the lip (about 1 mm) to create harmless micro trauma without actually puncturing the lip 1200. This results in activating cell regeneration deeply within the lip, as opposed to only on the surface of the lips 1200. This works to increase the overall volume of the lips by targeting a deeper portion of the mucosa and making it thicker through new cell growth and enhanced collagen production.

Turning now to FIG. 11, the housing 102 also encapsulates a power source 1110, an activation button 124, a USB port 400, and a circuit board 1112 to regulate aspects of the vibratory motion. The power source 1110 may include a battery, an electrical outlet or other forms of energy, providing the necessary power for the motor 1106 and vibrating member 1108 to supply the vibrations. In one non-limiting embodiment, the power source 1110 comprises a battery have a volt range between 1.5 Volts Direct Current to 8 Volts Direct Current. In another non-limiting embodiment, the circuit board 1112 has a load current between about 0.2 amps to 0.8 amps.

The activation button 124 can be disposed anywhere on the housing 102. The activation button 124 is configured to interrupt the flow of energy to the circuit and to the vibrating member 1108, i.e., move a switch from an off, or incomplete circuit position, to an on, or completing an electrical circuit. In some embodiments, the activation button 124 and/or switch translatably coupled thereto may be configured to remain in one state unless actuated—either completely on or completely off. In another embodiment, a lighted switch cover 1104 overlays the activation button/switch 124.

Further, an outer case 1100 encapsulates the housing 102, providing additional protection against impact, moisture, and debris. In some embodiments, the outer case 1100 may form a charge opening 402 and a switch opening 1102 that enables access to the USB port 400 and the activation button, respectively. In one non-limiting embodiment, the outer case 1100 is fabricated from casted 6061 aluminum. Though other rigid, waterproof materials may also be used.

Figure 18:
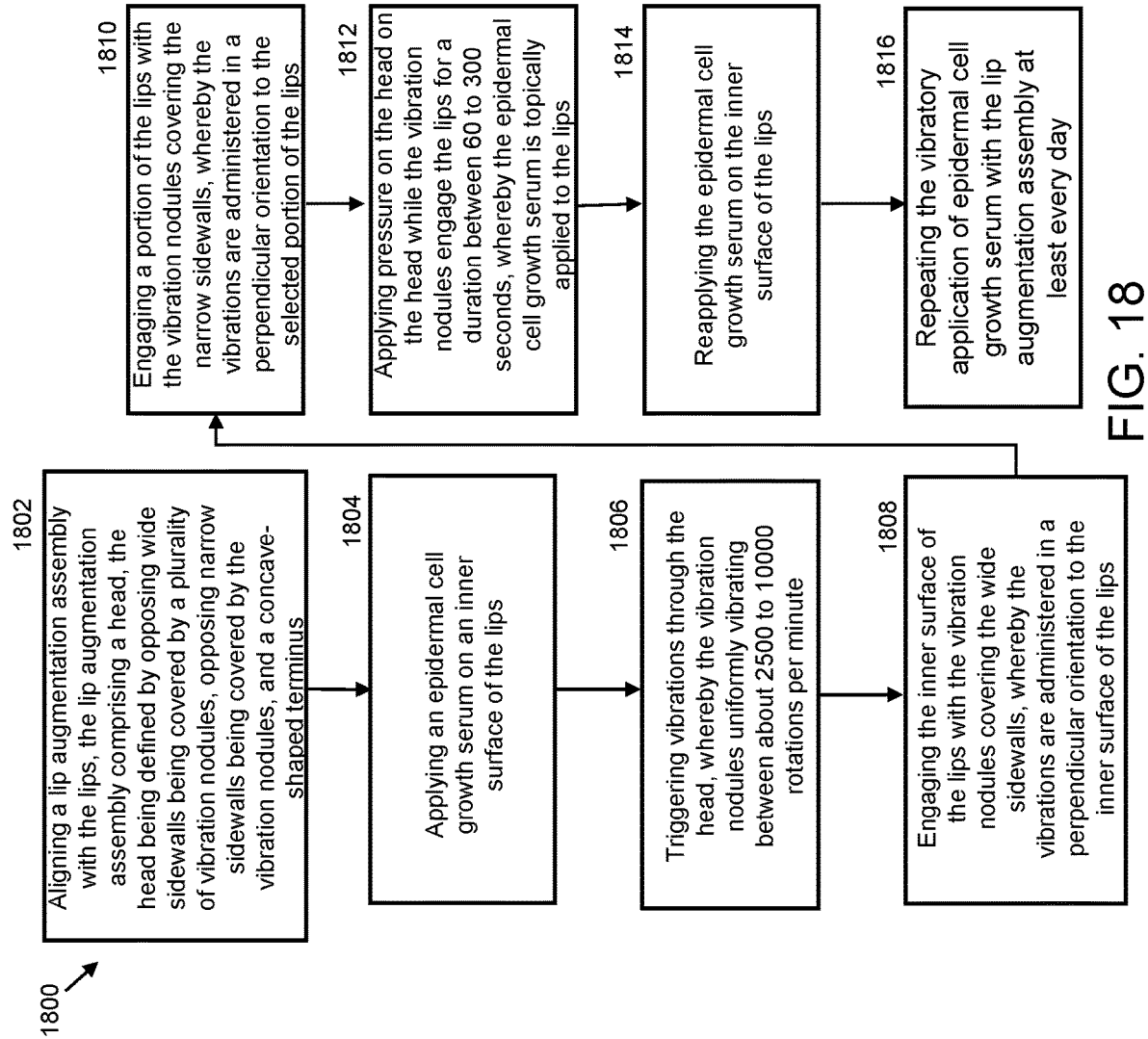
FIG. 18 is a flowchart referencing an exemplary method for plumping a selected segment of the lips, in accordance with an embodiment of the present invention.

FIG. 18 will be described in conjunction with the process flow chart. Although FIG. 18 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted for the sake of brevity. In some embodiments, some or all of the process steps included in FIG. 18 can be combined into a single process.

The method 1800 includes applying a specially formulated epidermal cell growth serum to the inner surface 1202 of the lips and wrapping the inside portion of the lips (the labial mucosa) around the vibrating head 110. The method 1800 further includes applying pressure from the textured head 110 to the labial mucosa with the user's fingers for 60-300 seconds every other day. This helps promote uniform semi-permanent augmentation of the lip tissue by creating micro trauma in the labial mucosa which promotes the growth (proliferation) and regeneration of epidermal cells in the labial mucosa and the subsequent increase in dermal thickness of the labial mucosa with continued use. The device and method 1800 can be used every other day until the desired lip volume is achieved. Once the desired lip volume is achieved, the method 1800 can be used once per week, but topical application of the serum 1204 is used daily to maintain the augmented lip volume.

As discussed above, FIG. 18 references a flowchart for an exemplary method 1800 of selectively plumping segments of the lips. The method 1800 includes an initial Step 1802 of aligning a lip augmentation assembly with the lips, the lip augmentation assembly comprising a head, the head being defined by opposing wide sidewalls 302a, 302b being covered by a plurality of vibration nodules, opposing narrow sidewalls being covered by the vibration nodules, and a concave-shaped terminus.

The method 1800 may further comprise a Step 1804 of applying an epidermal cell growth serum on an inner surface of the lips. The epidermal cell growth serum 1204 is applied to the lip mucosa both before and after pressing the vibrating head 110 to the lip mucosa. The serum 1204 contains ingredients that promote faster proliferation of epidermal cells, such as plant stem cells and/or growth factors such as Epidermal Growth Factor (EGF) and Basic Fibroblast Growth Factor and (BFGF). A Step 1806 includes triggering vibrations through the head 110, whereby the vibration nodules 122a-n uniformly vibrating between about 2500 to 10000 rotations per minute.

In some embodiments, a Step 1808 comprises engaging the inner surface of the lips with the vibration nodules covering the wide sidewalls, whereby the vibrations are administered in a perpendicular orientation to the inner surface of the lips. In this Step 1808, the head 110 is positioned against the inner surface 1202 of the lips 1200, so as to allow the vibrations from the vibration nodules 122a-n to vibrate the lips in a perpendicular or an "up and down" motion.

For example, FIG. 12 illustrates a perspective side view of the vibrating head 110 fully inserted into the mouth and pressing against the inner surface 1202 of the lips 1200. FIG. 13 is a perspective side view of the assembly 100 augmenting an upper lip, showing the vibrating head 110 pressing against the inner surface of the upper lip. And FIG. 14 is a perspective side view of the assembly 100 augmenting a lower lip, showing the vibrating head 110 pressing against the inner surface of the lower lip.

Figure 15:
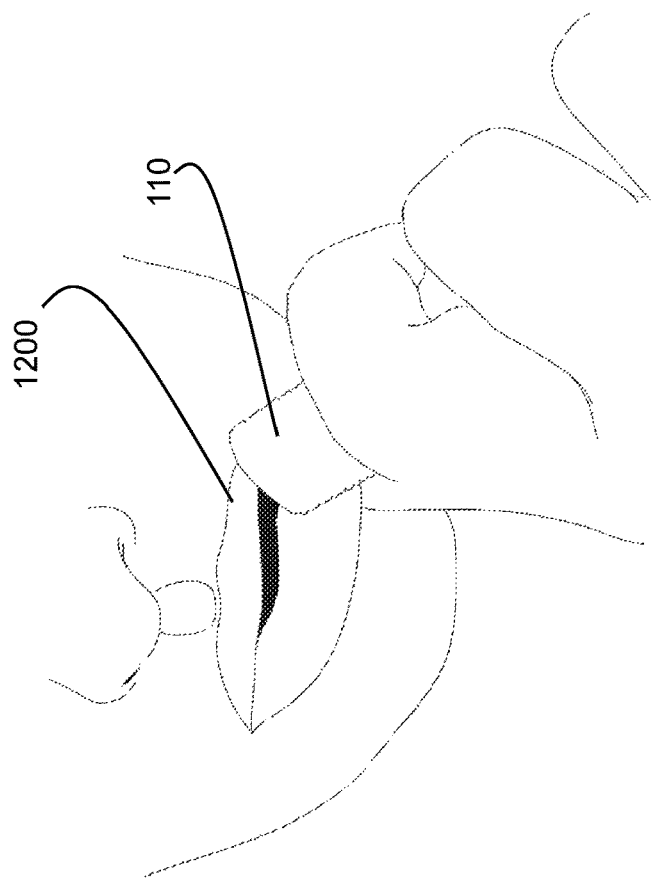
FIG. 15 is a front view of the lip augmenting assembly augmenting the left side of the lips, showing the vibrating head pressing against the inner surface of the left side of the lips, in accordance with an embodiment of the present invention.
Figure 17:
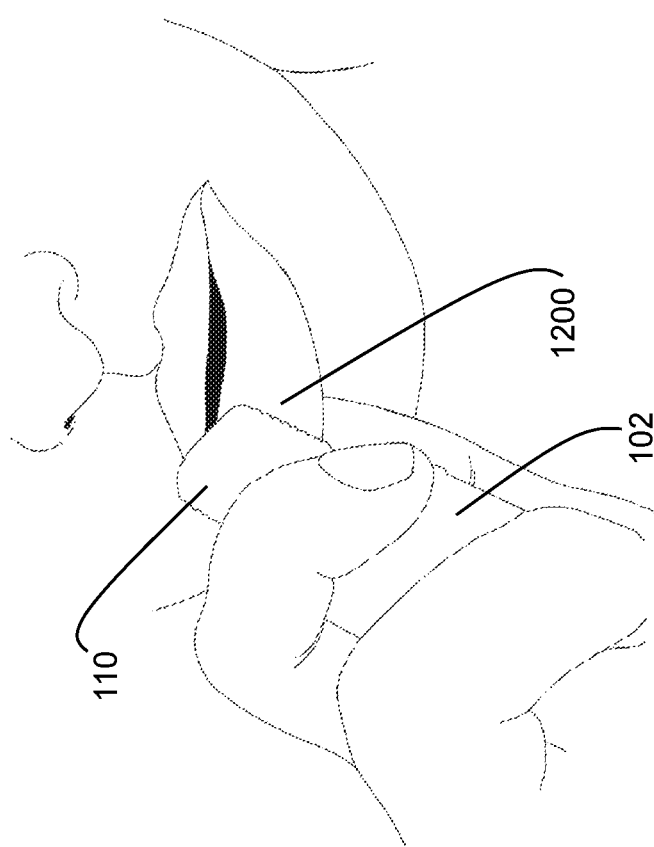
FIG. 17 is a front view of the lip augmenting assembly augmenting the right side of the lips, showing the vibrating head pressing against the inner surface of the right side of the lips, in accordance with an embodiment of the present invention.
Figure 16:
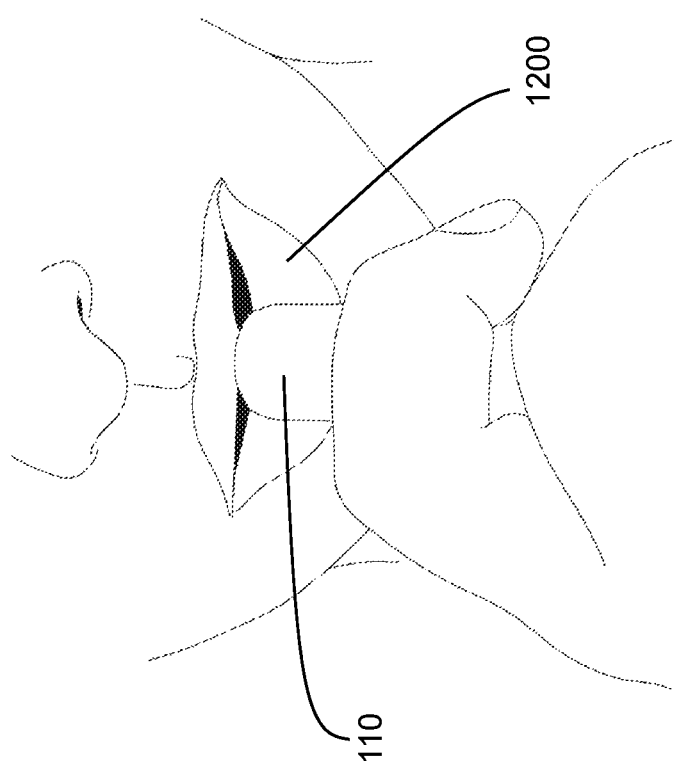
FIG. 16 is a front view of the lip augmenting assembly augmenting the center of the lips, showing the vibrating head pressing against the inner surface of the center of the lips, in accordance with an embodiment of the present invention.

A Step 1810 includes engaging a portion of the lips with the vibration nodules covering the narrow sidewalls, whereby the vibrations are administered in a perpendicular orientation to the selected portion of the lips. By engaging the lips with the narrow sidewall of the head 110, a segment of the lips may be augmented, while the remaining portion of the lips is left alone (FIGS. 15-17). Whereas, the wide sidewall of the head 110 fully engages the entirety of the lips, as described in FIGS. 12-14.

FIG. 15 is a front view of the assembly 100 augmenting the left side of the lips. FIG. 16 is a front view of the assembly 100 augmenting the center of the lips. FIG. 17 is a front view of the assembly 100 augmenting the right side of the lips, showing the vibrating head 110 pressing against the inner surface of the right side of the lips. In each of these lip augmentation manipulations, a portion of the lip is engaged by the vibration nodules 122a-n on the vibrating head 110 to augment a segment of the lips 1200.

In some embodiments, a Step 1812 may include applying pressure on the head on the head while the vibration nodules engage the lips for a duration between 60 to 300 seconds, whereby the epidermal cell growth serum is topically applied to the lips. The first end 104 of the housing 102 provides an effective grip to control pressure and angle of contact between the vibrating head 110 and the lips. The head 110 is manipulated against the desired segment of the lips for augmentation thereof.

A Step 1814 comprises reapplying the epidermal cell growth serum on the inner surface of the lips. The serum 1204 is used to promote faster regeneration and growth of the cells in the lip mucosa after the pressure of the mechanical vibration and the grid-shaped vibration nodules 122a-n of the head 110 of the device create harmless micro trauma to the mucosa which triggers the epidermal cell growth effect and promotes new collagen production. The serum 1204 must be used in combination with the vibrating head 110, as well as daily to increase the lip augmentation effect of the device by promoting cell proliferation of the mucosa of the lips. A final Step 1816 includes repeating the vibratory application of epidermal cell growth serum with the lip augmentation assembly at least every other day.

Although the invention is illustrated and described herein as embodied in a Lip Augmentation Assembly and Method of Selectively Plumping Segments of the Lips, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

What is claimed is:

1. A lip augmentation assembly comprising:
    a housing having a first end, a second end opposite the first end, a housing length separating the first and second ends of the housing, an activation button disposed thereon along the housing length, and a head of an oval shape and including a lower end structure with a bottom end proximal to the second end of the housing and tapering in width until terminating at an upper end where a head length begins and with the head length spanning from the upper end of the lower end structure until terminating at a terminus of the head, with an outer surface, an upper wide sidewall defining an upper side spanning a wide sidewall width of the head along the head length and on the outer surface of the head, a bottom wide sidewall defining a bottom side opposing the upper side of the head that spans the wide sidewall width of the head uniformly along the entire head length and on the outer surface of the head, and opposing narrow sidewalls that are curved and extend between the upper and bottom sides of the head, the wide sidewalls of the head flatter than the curved opposing narrow sidewalls, the housing encapsulating an electric motor having a vibrating member surrounded by the head and operably coupled to the activation button, and the width of the upper and bottom sides of the head less than the width of the bottom end of the lower end structure; and
    a plurality of vibration nodules covering the upper side of the head in a tightly spaced configuration with 6 to 64 of the plurality of vibration nodules disposed within an area of 6 to 64 per centimeter squared and covering the bottom side of the head in a tightly spaced configuration, each of the plurality of vibration nodules spanning in a direction outwardly away from the outer surface of the head and terminating into a rounded tip to collectively, on the upper and bottom sides of the head respectively, define a lip application surface, and whereby the head is sized to be inserted into a user's mouth with the lips of the mouth disposed on the lip application surface.

2. The lip augmentation assembly according to claim 1, wherein: the head is cylindrical along the head length.

3. The lip augmentation assembly according to claim 1, wherein:
    the plurality of vibration nodules are disposed on the upper and bottom sides of the head to define an upper-side termination point and a bottom-side termination point defined on each of the upper and bottom sides of the head, wherein the upper-side and bottom-side termination points on each of the upper and bottom sides of the head are aligned with one another.

4. The lip augmentation assembly according to claim 3, wherein:
    the upper-side termination point and the bottom-side termination point are both disposed along the head length a distance greater than 50% the head length.

5. The lip augmentation assembly according to claim 4, further comprising:
    a nodule application length separating the upper-side termination point and the bottom-side termination point on each on the upper and bottom sides of the head, respectively, and defining a nodule application length midpoint and with a first nodule plane spanning through the nodule application length midpoint, wherein the plurality of vibration nodules are symmetrically disposed with respect to one another about the first nodule plane.

6. The lip augmentation assembly according to claim 5, wherein:
    the plurality of vibration nodules are symmetrically disposed with respect to the midpoint of the width of the head.

7. A lip augmentation assembly comprising:
    a housing having a first end, a second end opposite the first end, a housing length separating the first and second ends of the housing, and an activation button disposed thereon along the housing length, the housing encapsulating an electric motor having a vibrating member surrounded by a head and operably coupled to the activation button;
    the head defining an upper side and a bottom side opposing the upper side of the head, the upper side spanning a width of the head and the bottom side spanning the width of the head,
    the head further defining opposing wide sidewalls and opposing narrow sidewalls that are curved and extend between the upper and bottom sides and defining a concave-shaped terminus opposite the first end of the housing and extending inwardly from an end of the opposing wide sidewalls and opposing narrow sidewalls, the wide sidewalls of the head flatter than the curved opposing narrow sidewalls; and
    a plurality of vibration nodules being arranged in a grid-shaped pattern of aligned rows and columns on the wide sidewalls of the head and with a portion of the plurality of vibration nodules being disposed proximal to the end of the opposing wide sidewalls and opposing narrow sidewalls, each of the plurality of vibration nodules spanning in a direction outwardly away from the wide sidewalls of the head and terminating into a rounded tip with a radius of curvature ranging from 0.55 mm to 1.9 mm, the plurality of vibration nodules collectively, on the upper and bottom sides of the head respectively, defining a lip application surface, and whereby the head is sized to be inserted into a user's mouth with the lips of the mouth disposed on the lip application surface.

8. The lip augmentation assembly according to claim 7, wherein:

the plurality of vibration nodules are disposed on the upper and bottom sides of the head to define an upper-side termination point and a bottom-side termination point defined on each of the upper and bottom sides of the head, wherein the upper-side and bottom-side termination points on each of the upper and bottom sides of the head are aligned with one another.

9. The lip augmentation assembly according to claim 8, further comprising:

a nodule application length separating the second end of the housing and the upper-side termination point and the bottom-side termination point, respectively and defining a nodule application length midpoint and with a first nodule plane spanning through the nodule application length midpoint, wherein the plurality of vibration nodules are symmetrically disposed with respect to one another about the first nodule plane.

10. The lip augmentation assembly according to claim 7, wherein:

the wide sidewalls of the head are flat and have a width of 21.30 millimeters.

11. The lip augmentation assembly according to claim 7, wherein:

the narrow sidewalls of the head are rounded and have a width of 16.36 millimeters.

12. The lip augmentation assembly according to claim 7, wherein:

the plurality of vibration nodules are spaced apart 0.1 to 0.2 millimeters from each other.

13. The lip augmentation assembly according to claim 7, wherein:

the housing encapsulates a power source, a circuit board, and a lighted button cover, the housing further forming a USB port.

14. The lip augmentation assembly according to claim 13, further comprising:

an outer case forming a charge opening enabling passage to the USB port, and a switch opening enabling passage to the activation button.

15. The lip augmentation assembly according to claim 7, wherein the head further comprises:

a lower end structure with a bottom end proximal to the second end of the housing and tapering in width until terminating at an upper end where a head length begins and with the head length spanning from the upper end of the lower end structure until terminating at the terminus of the head, the width of the upper and bottom sides of the head less than the width of the bottom end of the lower end structure.

16. A method of selectively plumping segments of a user's lips, the method comprising:

aligning a lip augmentation assembly with the lips of a user's mouth such that a head of the lip augmentation assembly is inserted into the user's mouth and with the lips of the user's mouth disposed on a plurality of vibration nodules on opposing wide sidewalls of the head, respectively, the head of an oval shape and defining the opposing wide sidewalls covered by the plurality of vibration nodules, the opposing narrow sidewalls, and a terminus, the head sidewalls defining a uniform width spanning from an upper end of a lower end structure of the head and until terminating at the terminus of the head;

applying an epidermal cell growth serum on an inner surface of the lips of the user's mouth;

triggering vibrations through the head, whereby the vibration nodules uniformly vibrate between 2500 to 10000 rotations per minute;

engaging the inner surface of the lips of the user's mouth with the vibration nodules covering the opposing wide sidewalls, whereby the vibrations are administered in a perpendicular orientation to the inner surface of the lips of the user's mouth;

engaging a portion of the lips of the user's mouth with the vibration nodules covering the opposing narrow sidewalls, whereby the vibrations are administered in a perpendicular orientation to the selected portion of the lips of the user's mouth;

applying pressure on the opposing wide sidewalls of the head while the vibration nodules engage the lips of the user's mouth for a duration between 60 to 300 seconds, whereby the epidermal cell growth serum is topically applied to the lips of the user's mouth;

reapplying the epidermal cell growth serum on the inner surface of the lips of the user's mouth; and repeating the vibratory application of epidermal cell growth serum with the lip augmentation assembly at least every day.

* * * * *